United States Patent [19]

Mabilat et al.

[11] Patent Number: 5,723,344
[45] Date of Patent: Mar. 3, 1998

[54] DEVICE FOR THE CAPTURE OF TARGET MOLECULES, AND CAPTURING PROCESS USING THE DEVICE

[75] Inventors: Claude Mabilat, Villeurbanne; Philippe Cros, Lyons; Bernard Mandrand, Villeurbanne; Marie-Hélène Charles, Condrieu; Marie-Noëlle Erout, Sainte Foy les Lyon; Christian Pichot, Corbas, all of France

[73] Assignee: Bio Merieux, Marcy l'Etoile, France

[21] Appl. No.: 264,996

[22] Filed: Jun. 24, 1994

[30] Foreign Application Priority Data

Jun. 25, 1993 [FR] France .................... 93 07797

[51] Int. Cl.⁶ ............... G01N 33/543; G01N 33/544; C12Q 1/68
[52] U.S. Cl. .............. 436/518; 422/57; 435/6; 435/7.1; 435/7.5; 435/7.92; 435/7.94; 435/287.2; 435/287.9; 435/975; 436/524; 436/528; 436/531; 436/532; 436/534; 436/807
[58] Field of Search .................. 435/6, 7.5, 7.1, 435/7.92, 7.94, 975, 287.2, 287.9; 436/518, 524, 528, 531, 532, 534, 807; 525/54.1; 422/57, 60

[56] References Cited

U.S. PATENT DOCUMENTS

| | | |
|---|---|---|
| 4,070,348 | 1/1978 | Kräemer et al. . |
| 4,228,152 | 10/1980 | Ferruti et al. . |
| 4,478,914 | 10/1984 | Giese . |
| 4,657,873 | 4/1987 | Gadow et al. ............... 436/532 |
| 4,737,544 | 4/1988 | McCain et al. ............... 525/54.1 |
| 4,894,325 | 1/1990 | Englehardt et al. ............... 435/6 |
| 5,200,462 | 4/1993 | Sutton et al. . |
| 5,270,193 | 12/1993 | Eveleigh ............... 436/532 |

FOREIGN PATENT DOCUMENTS

| | | |
|---|---|---|
| 91/08307 | 6/1991 | WIPO . |
| 91/19812 | 12/1991 | WIPO . |
| 93/02216 | 2/1993 | WIPO . |

OTHER PUBLICATIONS

Gray, 1979. Elisa methodology for polysaccharide antigens: protein coupling of polysaccharides for adsorption to plastic tubes. J. Immunolog. Meth. 28: 187–192.

*Primary Examiner*—Paula K. Hutzell
*Assistant Examiner*—James L. Grun
*Attorney, Agent, or Firm*—Oliff & Berridge PLC

[57] ABSTRACT

Device for capturing a target molecule for the purpose of detecting it and/or assaying it, including a solid support on which is immobilized a ligand, the ligand being provided in the form of a conjugate resulting from the covalent coupling of a polymer with a plurality of molecules of the ligand. The polymer is an N-vinylpyrrolidone copolymer, and the conjugate is immobilized on the solid support by adsorption.

When the ligand is capable of forming a complex with the target, the device is specific for a given target. When the device comprises, in addition, a bifunctional reagent capable of forming a complex, on the one hand, with the ligand and, on the other hand, with the target, the support on which the ligand is immobilized constitutes a universal capturing system.

15 Claims, No Drawings

DEVICE FOR THE CAPTURE OF TARGET MOLECULES, AND CAPTURING PROCESS USING THE DEVICE

The subject of the present invention is a device for improving the capture of target molecules and a capturing process using the said device.

It is a common practice to use supports on which are immobilized ligands, for example proteins, haptens, peptides, polypeptides, antibodies or polynucleotides to capture target molecules (biological molecules or the like), for the purpose of detecting them and/or assaying them, especially in the performing of diagnostic assays.

One of the main concerns in performing such assays is to improve the capture of molecules in order to increase the sensitivity of the tests.

In this respect, Patent Application WO 91/08307 describes a system in which a first oligonucleotide and a capture probe are covalently attached to a water-soluble polymer and the conjugate thus formed is, after capturing the target, immobilized on a solid support by combination with a second oligonucleotide which is complementary to the first, and which has previously been covalently attached to the solid support.

The applicant has now found a new device and a process for using this device to improve the capture of target molecules which advantageously simplify the system described in the abovementioned patent application.

According to the invention, the device comprises a solid support and a conjugate immobilized on the said solid support, the said conjugate resulting from the covalent coupling of a copolymer with a plurality of molecules of a ligand (at least 2 molecules of ligand), the said conjugate being immobilized directly on the solid support by passive adsorption. Of course, neither the ligand nor the polymer are capable of reacting with the solid support with formation of a covalent bond.

The subject of the invention is therefore a device for capturing a target molecule for the purpose of detecting it and/or assaying it, comprising a solid support on which is immobilized a ligand, characterized by the fact that the said ligand is provided in the form of a conjugate resulting from the covalent coupling of a polymer with a plurality of molecules of the said ligand, that the said polymer is an N-vinylpyrrolidone copolymer, and that the said conjugate is immobilized on the solid support by adsorption.

According to a first embodiment, the ligand is specific for the target molecule. In this embodiment, the ligand is especially chosen in order to be capable of forming a ligand/target-molecule capture complex. As an example, the complex can especially be represented by any antigen/antibody, antibody/hapten, hormone/receptor or chelator/chelated molecule pair, the polynucleotide/polynucleotide or polynucleotide/nucleic acid hybrids, and the like.

The ligand is for example a polynucleotide having a nucleotide sequence of about 5 to 100 nucleotides and sufficiently complementary to the nucleotide sequence of the nucleic acid fragment or polynucleotide to be captured to permit the hybridization of the said sequences under given conditions.

In another embodiment, the ligand is capable of forming a complex with a bifunctional reagent comprising an "anti-ligand" group, responsible for the formation of the complex with the ligand, and in which the said anti-ligand group is bonded, especially covalently, in a known manner, to a partner group for the target. The partner for the target is a group capable of binding with the target (by forming a target/partner complex) and is therefore capable of capturing the target, under the conditions of the assay, by establishing a bond which is sufficiently strong to ensure the target-partner inter-action, for example by covalency and/or by ionic inter-actions and/or by hydrogen bonds and/or by hydrophobic bonds. The ligand/anti-ligand complex can be, in this case, any pair mentioned above for the first embodiment, or alternatively a biotin/streptavidin or lectin/sugar complex or the like. In particular, the ligand/anti-ligand complex is a polynucleotide/polynucleotide hybrid. The partner/target complex is of the same type as the ligand/target complex mentioned above for the first embodiment. In this second embodiment, the system formed by the ligand attached to the solid support and by the bifunctional reagent makes it possible to immobilize, by a double capture phenomena, any target complementary to the partner group chosen for the production of the bi-functional reagent, and this system therefore constitutes a universal capturing device, that is to say one which can be used irrespective of the nature of the target molecule, by virtue of the use of a bifunctional reagent comprising an appropriate partner .group, as explained above.

The copolymer which can be used in the device according to the invention is not necessarily soluble in the aqueous or organic solvents compatible with the support, hut the conjugate should he. This polymer is preferably a copolymer having a molecular mass generally of between 1000 and 500000, for example between 10000 and 250000. The said copolymer may be a random, alternating, graft or block copolymer. N-vinylpyrrolidone copolymers, preferably bipolymers, are particularly used.

The copolymer results from the copolymerization of an N-vinylpyrrolidone monomer and an appropriate second monomer in order to permit the establishment of a covalent coupling between the ligand and the copolymer. For example, the second monomer may carry a reactive functional group such as aldehyde, epoxy, haloalkyl, primary amine, thiol, maleimide or ester, (preferably an N-hydroxysuccinimide ester functional group), or an activable functional group such as a carboxyl functional group (activable especially by formation of a hydroxy-succinimide ester) or such as a hydroxyl functional group (activable especially by cyanogen bromide). In particular, the two monomers are N-vinylpyrrolidone and N-acryloxysuccinimide. The copolymer comprises especially from 25 to 70%, as units, of units derived from N-vinylpyrrolidone.

The subject of the invention is also a process for improving the capture of biological molecules, in which the target molecule, in solution in a liquid vehicle, is brought into contact with a device as defined earlier under (known) conditions which make it possible to capture the target by formation of a capture complex of the ligand/anti-ligand type. In the first type of embodiment mentioned above, the anti-ligand is the target molecule. In the second embodiment, the anti-ligand is itself bonded to a partner of the target, such as an antibody (the target is then an antigen or a hapten), an antigen, a protein, a peptide or a hapten (the target is then an antibody), a polynucleotide (the target then contains a complementary polynucleotide), and the like.

The support and the process of the invention can be used especially in tests for the detection and quantification of a nucleotide sequence in a sample, for example by sandwich or "Reverse Dot" techniques. They can also be used in immunoassays (according to the direct, sandwich or competition technique) to capture a biological molecule.

The chemical composition of the copolymer is not a critical factor since the polymer makes it possible to couple a ligand for the formation of the conjugate and makes it possible to immobilize the latter on the solid support. By simple routine experiments, it is possible either to choose the satisfactory copolymer(s), permitting, in particular, good attachment of the conjugate, by passive adsorption, on the chosen solid support which it is desired to use, or to choose, from among the customary solid supports, those permitting good attachment, by passive adsorption, of the conjugate. Preferably, copolymers containing two different monomeric units, one of which is derived from N-vinylpyrrolidone, are used. These copolymers are called bipolymers in the description of the present application.

These various bipolymers can be obtained by the free radical route, by the ionic route or by group transfer reaction.

The term "polynucleotide" as used in the present application designates a linkage of at least 5 deoxyribonucleotides or ribonucleotides optionally comprising at least one modified nucleotide, for example at least one nucleotide comprising a modified base such as inosine, 5-methyldeoxycytidine, 5-dimethylaminodeoxpuridine, deoxyuridine, 2,6-diaminopurine, 5-bromodeoxyuridine or any other modified base permitting the hybridization. This polynucleotidemay also be modified at the level of the internucleotide bond (as for example the phosphorothioate, H-phosphonate or alkyl-phosphonate bonds), or at the level of the backbone such as for example the alpha-oligonucleotides (FR 2,607,507) or the PNAs (M. Egholm et al., J. Am. Chem. Soc., (1992), 114, 1895–1897). Each of these modifications can be taken in combination.

The term "solid support" as used here includes all the known materials on which a polynucleotide can be immobilized and which are used as supports in diagnostic tests, in affinity chromatography and in separation procedures. Natural or synthetic materials, chemically modified or otherwise, can be used as solid support, especially polysaccharides such as cellulose materials, for example paper, cellulose derivatives such as cellulose acetate and nitrocellulose, dextran; polymers such as polyvinyl chloride, polyethylene, polystyrene, polyacrylate, polyamide, or copolymers based on aromatic vinyl monomers, unsaturated carboxylic acid esters, vinylidene chloride, dienes or compounds having nitrile functional groups (acrylonitrile); vinyl chloride/propylene, or vinyl chloride/vinyl acetate copolymers; copolymers based on styrene or substituted derivatives of styrene; natural fibres such as cotton and synthetic fibres such as nylon; inorganic materials such as silica, glass, ceramic, quartz; latexes, that is to say colloidal aqueous dispersions of water-insoluble polymer; magnetic particles; and metallic derivatives.

Preferably, the solid support used in the present invention is polystyrene, a butadiene-styrene copolymer or a butadiene-styrene copolymer mixed with one or more polymers or copolymers chosen from styrene-acrylonitrile or styrene-methyl methacrylate copolymers, polypropylenes, polycarbonates and the like. Advantageously, the support of the present invention is a polystyrene or a styrene-based copolymer comprising between about 10 and 90% by weight of units derived from styrene.

The solid support according to the invention may be, without limitation, in the form of a microtitre plate, a sheet, a cone, a tube, a well, beads, particles or the like.

"Passive attachment" is understood to mean an attachment due to forces other than forces of covalent bonding.

The term "biological molecule" or "target" as used in the present invention includes nucleic acids such as DNA or RNA or fragments thereof, antigens, haptens, peptides, polypeptides, antibodies and the like.

The term "antibody" also includes antibody fragments, and antibodies obtained by modification or genetic recombination.

The term "hapten" designates a molecule of sufficient size to be immunogenic, but which, by coupling with a protein for example, permits, by immunization of animals, the production of antibodies recognizing the said molecule.

The formation of a conjugate resulting from the covalent coupling of a ligand, for example, a polynucleotide to a copolymer, can be carried out according to the so-called direct or indirect methods, which are known.

For example, in the case of a polynucleotide, according to the direct method, a polynucleotide is synthesized which has a reactive functional group at any site of the nucleotide chain such as for example, the 5' end or the 3' end, or on a base or on an internucleotide phosphate, or at position 2' of a sugar. The polynucleotide is then coupled to a polymer prepared beforehand and containing a reactive functional group complementary to the preceding one, that is to say permitting the formation of a covalent bond by reaction between the two complementary reactive functional groups, one carried by the polynucleotide and the other by the polymer. For example, in a known manner, primary amines can be coupled with an activated carboxylic acid or an aldehyde or alternatively a thiol functional group with a haloalkyl. Preferably, the reactive functional group of the polynucleotide for the coupling with the polymer is at the 5' or 3' end.

In the indirect coupling method, the polynucleotide and the polymer are each carriers of a reactive functional group, it being possible for these reactive functional groups to be identical or different from each other, these two functional groups not being complementary but being capable of reacting with an intermediate coupling agent which is a bifunctional reagent (homobifunctional if the two functional groups are identical or heterobifunctional if the two functional groups are different). Among the homobifunctional coupling agents, there may be mentioned DITC (1,4-phenylene diisothiocyanate), DSS (disuccinimidyl suberate) or the like. Among the heterobifunctional coupling agents, there may be mentioned SMCC (succinimidyl-4-(N-maleimidomethyl)cyclohexane-1-carboxylate), or SMPB (succinimidyl-4-(p-maleimidophenyl)butyrate) which are capable of reacting, on the one hand, with a primary amine and, on the other hand, with a thiol.

After coupling the ligand with the copolymer, the possible excess reactive functional groups of the copolymer are neutralized in a manner known per se. For example, the aldehyde groups in excess can be neutralized with a primary amine such as ethanolamine, the maleimide or haloalkyl groups can be neutralized with a thiol (such as thioethanolamine or dithiothreitol), and so on.

The subject of the invention is also a process for improving the capture of target molecules, in which the target molecule in solution in a liquid vehicle is brought into contact with a device as defined earlier (that is to say the solid support onto which the polymer/ligand conjugate is attached and, in the case of the second embodiment, the solid support onto which is attached the polymer/ligand conjugate and the anti-ligand/partner bifunctional reagent), under conditions permitting the formation of a ligand/anti-ligand the complex or the formation of a ligand/anti-ligand and target/partner complex. The conditions for forming such complexes are known per se.

The following examples illustrate the invention.

EXAMPLE 1

Synthesis And Characterization of the Bipolymers

The procedure below constitutes the general procedure for the copolymerization reactions.

Table 1 will later summarize the specific conditions for this synthesis.

In a 100 ml three-necked round-bottomed flask, purged with nitrogen, are mixed 50 ml of anhydrous dimethylformamide (ALDRICH; reference 22705-6), a quantity x, expressed in grams (g) of freshly distilled N-vinyl pyrrolidone (ALDRICH; reference V 340-9), as well as a quantity y (in grams) of N-acryloxysuccinimide (KODAK; reference 110 1690).

The reaction medium, heated to a temperature of 60° C., is stirred for 2 hours, with regular bubbling of nitrogen, in order to remove any traces of oxygen.

z g of 4',4'tazobis(4-cyanopentanoic) acid (FLUKA; reference 11 590) are dissolved in 1 ml of anhydrous dimethylformamide. This compound constitutes the trigger for the free radical polymerization reaction.

After a bubbling of nitrogen for 15 minutes, the trigger solution is added rapidly to the reaction medium. This constitutes the time zero for the polymerization.

The reaction is carried out at 60° C., with stirring, with slow and regular bubbling of nitrogen.

Samples are collected every 3 minutes.

To stop the reaction, a few grains of a polymerization inhibitor: hydroquinone (JANSSEN; reference 123-31-9) are added. The samples are then placed on ice.

Each of these samples is then analysed by gas chromatography (DI 200 chromatograph, ENICA 21 integrator, from the company DELSI INSTRUMENTS), using an SE 30 column (methylsilicone adsorbed onto Chromosorb 10%). This makes it possible to monitor to kinetics of the polymerization reaction, that is to say to know, at any instant, the quantity of residual monomers, and therefore the rate of conversion (relative to each monomer and overall).

Analysis conditions:

Air pressure=$H_2$ pressure=1 bar ($10^5$ Pa).
$N_2$ pressure=0.8 bar.
Oven temperature=175° C.
Temperature of the injector=temperature of the detector= 300° C.

After a reaction time denoted t and expressed in hours, the reaction medium is poured into a separating funnel, and then added dropwise into a beaker containing a large excess of ethyl ether (SDS, reference 440516), with vigorous stirring.

The polymer, formed during the reaction, precipitates in the form of fairly fine white crystals.

When all of the reaction medium has been precipitated, the ethyl ether solution is filtered on sintered glass No. 4. The polymer is washed with a large excess of ethyl ether and then dried for several hours in a vacuum oven, at room temperature.

To purify the polymer (removal of residual monomers as well as small molar masses), the latter is dissolved in N,N-dimethylforzamide (DMF) and then reprecipitated in ethyl ether.

The bipolymers thus obtained are preserved under an inert atmosphere, protected from moisture. They consist of units:

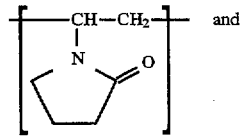 and

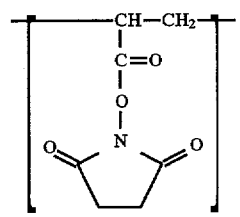

Table 1 below summarizes the conditions specific to each polymerization reaction.

TABLE 1

| Name of the bipolymers | x NVP (grams) | y NAS (grams) | C(*) moles/l | z AZCB (grams) | T (hours) | R (**) (%) |
|---|---|---|---|---|---|---|
| COPO1 | 2.22 | 0.84 | 0.5 | 0.074 | 20 | 55 |
| COPO2 | 2.78 | 4.22 | 1.0 | 0.148 | 20 | 90 |
| COPO3 | 1.14 | 2.54 | 0.5 | 0.074 | 20 | 90 |
| COPO4 | 0.23 | 0.50 | 0.1 | 0.015 | 20 | 90 |
| COPO5 | 2.28 | 5.08 | 1.0 | 0.148 | 20 | 90 |

(*)C represents the concentration of monomers in moles/liter, at the beginning of the reactions.
(**)R represents the conversion, expressed as percentage by mass, of the 2 starting monomers.
Abbreviations used in Table 1:
NVP = N-vinylpyrrolidone,
NAS = N-acryoxysuccinimide,
AZCB = 4,4'-azobis(4-cyanopentanoic) acid.

The characteristics of the bipolymers used in the present invention are summarized in Table 2.

TABLE 2

|  | Molecular mass (g/mole) (*) | Mole % of NAS in the final bipolymer (**) |
|---|---|---|
| COPO1 | 60,000 [10%] | 39 |
| COPO2 | 160,000 [2%] | 57 |
| COPO3 | 70,000 [2%] | 62 |
| COPO4 | 19,500 [2%] | 59 |
| COPO5 | 160,000 [2%] | 61 |

(*) The molecular masses were determined by light scattering (static method).
Study solvent: DMF/water = 90/10
Temperature: 20° C.
The figure in brackets represents the measurement error on the mass.
(**) This value was determined by assaying the N-hydroxy-succinimide (NHS) functional groups in the presence of an excess of $NH_4OH$ by UV spectroscopy at 260 nm with $e_{NHS}$ = 7100 l · $mole^{-1}$ · $cm^{-1}$ for the NHS in a water/DMF/$NH_4OH$(0.1M) mixture = 80/10/10.
The measurement error is 5%.

Table 3 gives the chemical shifts by nuclear magnetic resonance (NMR) of the various carbons of the bipolymer. The carbons are identified by the number as described in the schematic representation below:

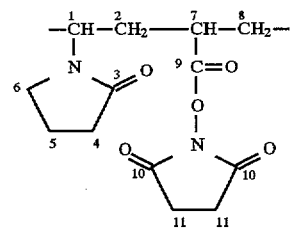

TABLE 3

| Position of the carbon | Chemical Shift |
|---|---|
| 1 | 48 (broad signal) |
| 2 | 34 (broad signal) |
| 3 | 175–177.5 (multiplet) |
| 4 | 32.2 (broad signal) |
| 5 | 19 (singlet) |
| 6 | 42 (broad signal) |
| 7 | 38.5 (broad signal) |
| 8 | 34 (broad signal) |
| 9 | 163.2 (singlet) |
| 10 | 171 and 170.9 (doublet) |
| 11 | 26.4 and 26.65 (doublet) |

Solvent: deuterated DMF.
Internal reference: dioxane with a signal at 67.8 ppm.

The chemical shifts are given in parts per million (ppm).

Coupling of Polynucleotides With Bipolymers

The polynucleotides used are synthetic oligodeoxyribonucleotides prepared with an Applied Biosystems model 394 automatic synthesizer according to the manufacturers procedure.

These oligonucleotides possess, at their 5' end, an $NH_2$ aliphatic arm prepared according to the method described in Patent Application WO 91/19812.

Via the ester functional groups Of the N-hydroxysuccinimide, there is direct reaction on the amine-containing arm at the 5' end of the oligonucleotide to form an amide bond.

The general coupling procedure is the following: An aqueous solution containing 32 nmol of oligonucleotides is poured into an Eppendorf tube, and then evaporated in a vacuum centrifugation evaporator.

The dry residue is taken up in 50 µl of 0.1M borate buffer pH=9.3 and then 400 µl of DMF are added.

50 µl of a solution of the bipolymer at 1 mg/ml in DMF (SDS, reference 340216) are added to this solution.

The Eppendorf tube containing the reaction medium is stirred for 16 hours in a heating Eppendorf tube stirrer heated to a temperature of 37° C.

The mixture (DMF/water) is then evaporated with the vacuum centrifugation evaporator.

The dry residue is taken up in 50 µl of distilled water, in order to be analysed by capillary electrophoresis.
Experimental conditions for the separation by capillary electrophoresis in free solution:
Apparatus: 270 A-HT marketed by the company APPLIED-BIOSYSTEMS.
Silica capillary 72 cm long (APPLIED-BIOSYSTEMS, Ref. 0602-0014).
Separating electrolyte: 50 mM sodium carbonate buffer, pH=9.6.
Applied voltage: 20 kilovolts.
Temperature: 40° C.
Injection at the anode.
Detection at the cathode, by UV spectroscopy at 260 nm (maximum wavelength of absorption for the oligonucleotide).

The bipolymer-oligonucleotide conjugate is then purified by gel permeation chromatography (GPC) under the following conditions:
WATERS Ultra Hydrogel 500 column.
0.1M phosphate buffer pH=6.8.
Detection by UV spectroscopy at 260 nm.
Flow rate 0.5 ml/min.

After purification, the conjugate in saline solution is dialysed overnight at +4° C. in order to remove the salt. The water is removed in the vacuum centrifugation evaporator. The dry residue is taken up in 1 ml of distilled water and stored in a freezer at a temperature of –20° C.

The list of the oligonucleotides used for the coupling to a bipolymer is given below.

The characteristics of the bipolymer-oligonucleotide conjugates are given in Table 4 below:

TABLE 4

| Conjugate | Bipolymer | SEQ ID No. (a) | Yield (b) | Tr (c) | Me (d) | Concentration (e) |
|---|---|---|---|---|---|---|
| CJOA | COPO1 | 2 | 60 | 10.03 | 9.8 | 15.1 |
| CJOB | COPO1 | 3 | 40 | 10.10 | 9.9 | 10.6 |
| CJOC | COPO3 | 2 | 50 | 10.50 | 10.2 | 15.5 |
| CJOD | COPO3 | 4 | 46 | 10.27 | 9.9 | 2.0 |
| CJOE | COPO3 | 5 | 53 | 10.01 | 10.1 | 12.8 |
| CJOF | COPO3 | 6 | 40 | 10.07 | 10.0 | 4.0 |
| CJOG | COPO3 | 1 | 48 | 10.36 | 9.9 | 2.5 |
| CJOH | COPO4 | 2 | 56 | 10.12 | 9.8 | 15.0 |
| CJOI | COPO5 | 2 | 50 | 10.25 | 10.0 | 14.0 |

(a) The oligonucleotides have the following sequences (from 5' to 3'):

| | |
|---|---|
| SEQ ID No. 1: TCATCCACCT GGCATTGGAC TGCCATAACC ATGAGTG | 37 |
| SEQ ID No. 2: TCTAATCCTG TTTGCTCCCC | 20 |
| SEQ ID No. 3: GATGAGCTAT ATGAGAACGG TA | 22 |
| SEQ ID No. 4: TTAACTTTAC TCCCTTCCTC CCCGCTG | 27 |
| SEQ ID No. 5: TCAATGAGCA AAGGTA | 16 |
| SEQ ID No. 6: GGTCCTATCC GGTATTAGAC CCAGTTTCC | 29 |

These oligonucleotides possess at their 5' end an aliphatic arm with an $NH_2$ functional group, prepared according to the method described in WO 91/19812.
(b) The coupling yield, calculated by integrating the peaks in GPC, is the ratio, by high-performance liquid chromatography (HPLC), of the surface area of the peak for the conjugate to the sum of the surface areas of the peak for the conjugate and the non-coupled oligonucleotide. It is given in %.
(c) Tr represents the retention time in GPC under the conditions described in the preceding paragraph. It is given in minutes.
(d) Me represents the retention time given in minutes under the conditions for separation in capillary electrophoresis which are described in the preceding paragraph.
(e) The concentration of the oligonucleotide is given in picomoles per ml, determined by UV spectrometry, by measuring the absorbance at 260 nm, knowing the molar extinction coefficient of the oligonucleotide at the same wavelength.

EXAMPLE 2

Detection of nucleic acids from *Escherichia coli* by the sandwich technique using oligonucleotides coupled to bipolymers as capture probe This example describes the signal and sensitivity gains obtained by using an oligonucleotide/NVP-NAS bipolymer conjugate as compared with a system where the capture probe consists of the oligonucleotide alone.

The model is the detection, by hybridization, of the taxonomic group *Escherichia coli* and Shigella. The target is the 16S ribosomal RNA (rRNA) of this group. The capture probe G3 (SEQ ID No. 4), coupled to the bipolymer, is complementary to the nucleotides 440 to 466 of the *Escherichia coli* 16S sequence determined by Brosius J. M., Palmer L. Kennedy P. J. Noller H. F. (1978) Proc. Natl. Acad. Sci. USA, 75, pages 4801–4805. The detection probe G1 (SEQ ID No. 5) consists of the sequence specific for the targeted taxon and thus differentiates it from the other bacterial species. It is conjugated with alkaline phosphatase as described in Patent WO 91/19812.

The hybridization of the rRNA of a target bacterium was performed according to the non-radioactive detection method described in Patent WO 91/19812. The following procedure is carried out automatically in the automaton VIDAS (BIOMERIEUX trademark). The following steps are performed automatically.

The reaction is carried out in the support called SPR (BIOMERIEUX-VITEK trademark) ("Solid Phase Receptacle") which is a conical support produced from a butadiene-styrene copolymer sold under the name K resin. The various reagents are placed in a strip with several wells and the various steps take place in the SPR which serves as a pipette. The sandwich hybridization reaction described in the procedure below takes place on the inner wall of the cone.

On the inner wall of the SPR is passively attached either the capture oligonucleotide G3, or comparatively the oligonucleotide G3-bipolymer conjugate (CJOD, Table 4). The concentration used in both cases is 1 ng/µl of oligonucleotides in a volume of 300 µl of 4×PBS solution (200 mM sodium phosphate pH 7.0, 600 mM NaCl). After a night at room temperature or two hours at 37° C., the cones are washed twice with a PBS Tween solution (1×PBS, Tween 20:0.5% (Merck 822184)), and then dried under vacuum. The strip contains all the reagents necessary for the detection, that is to say: 200 µl of a solution at 0.1 ng/µl of oligonucleotide G1-alkaline phosphatase detection conjugate, twice 600 µl of PBS Tween washing solution and a substrate cuvette. In the first well of the strip is placed a volume less than or equal to 100 µl containing the target in a buffer: PBS salmon (150 mM sodium phosphate, pH 7.0, 450 mM NaCl+0.1 mg/ml salmon sperm DNA (Sigma D 9156)). After incubation, 40 minutes, of the cone with the mixture of biological molecule plus detection probe, the cone is washed twice with a solution of PBS Tween. 250 µl of MUP (4-methylumbelliferyl phosphate) Substrate in solution in diethanolamine buffer are aspirated into the cone, then released into a reading cuvette. The apparatus measures the fluorescent signal expressed in RFU (relative fluorescence units) for the cuvette. The total time is 1 h 30 minutes.

Various hybridization targets were tested comparatively: either whole bacteria (*Escherichia coli* K-12HB101) in exponential growth phase, or purified rRNA (Boehringer Mannheim, reference 206 938), or a synthetic target called C1 complementary to the capture and detection oligonucleotides and of coordinates 437–497 corresponding to the sequence:

SEQ ID No. 7: TTTCAGCGGG GAGGAAGGGA GTAAAGT-
TAA TACCTTTGCT CATTGACGTT ACCCGCAGAA G    61

In the case of bacteria, the rRNA is directly extracted in the automaton by addition of sodium hydroxide up to a final concentration of 0.18N in 1 min followed by an immediate neutralization by addition of an equivalent quantity of acetic acid of the same molarity. A range of concentrations of each target was tested: from $10^{12}$ to $10^8$ copies of pure rRNA or of synthetic target, from $10^8$ to $10^4$ bacteria (ensuring in this latter case that when the number of rRNA in exponential growth phase is $10^4$ per bacterium, the range of rRNA target actually hybridized is $10^{12}$ to $10^8$ copies).

The results are summarized in Table 5.

TABLE 5

| Capture | $10^{12}$ | $10^{11}$ | $10^{10}$ | $10^9$ | $10^8$ |
|---|---|---|---|---|---|
| Synthetic target C1[a] | | | | | |
| G3 | 11030 | 5641 | 530 | 56 | 9 |
| CJOD | 10238 | 7644 | 1178 | 125 | 45 |
| Ribosomal RNA[a] | | | | | |
| G3 | 1200 | 215 | 36 | 8 | 8 |
| CJOD | 11242 | 6030 | 785 | 89 | 27 |

| | Bacteria[b] | | | | |
|---|---|---|---|---|---|
| Capture | $10^8$ | $10^7$ | $10^6$ | $10^5$ | $10^4$ |
| G3 | 3040 | 181 | 27 | 10 | 10 |
| CJOD | 11586 | 4326 | 557 | 66 | 17 |

[a]: the detection levels are expressed in RFU (relative fluorescence units) for a quantity of target expressed as the number of copies or number of molecules.
[b]: the detection levels are expressed in RFU for a quantity of target expressed as the number of bacteria lysed, knowing that a bacterium in exponential growth phase contains on average 10,000 ribosomal RNAs.

The use of the oligonucleotide-bipolymer conjugate clearly improves the intensity of the hybridization signal and the sensitivity on the whole target (pure or bacteria-extracted rRNA).

The improvement is of the order of a factor of 100 in sensitivity with a background value of 10–15 RFU. It is evident from this experiment that there is no difference in behaviour between pure rRNA and bacteria lysed with sodium hydroxide, that is to say that the lysis is effective and that the bacterial constituents other than the target do not interfere with the test.

In the case of the synthetic target, the sensitivity gain is lower. Because of its smaller size (61 bases), the steric hindrance between the target and the oligonucleotide on the support is reduced, which explains the differences observed between this synthetic target and the ribosomal RNA.

EXAMPLE 3

Detection of nucleic acids of the tuberculosis complex by the sandwich technique using oligonucleotides coupled to bipolymers as capture probe This example describes the signal and sensitivity gains obtained by the use of an oligonucleotide-bipolymer conjugate compared with a system where the capture probe consists of the oligonucleotide alone.

The model is the detection, by hybridization, of the taxonomic group "tuberculosis complex". The target is the 16S ribosomal RNA of this group. The capture probe E220 (SEQ ID No. 2) coupled to the bipolymer is complementary to the nucleotides 773 to 792 of the *Escherichia coli* 16S sequence or 863–882 of the *Mycobacterium tuberculosis* 16S sequence determined by Suzuki Y., Nagata A., Oho Y. and Yamada T. (1988), J. Bacteriol., 170, pages 2886–2889. The complementarity of E220 to the sequences of these two phylogenetically distant species is due to the fact that this unit is preserved in all eubacteria. The detection probe bovis310 consists of the sequence specific for the tuberculosis complex taxonomic group covering *M. tuberculosis, M. bovis, M. bovic BCG, M. africahum, M. microti* and thus differentiates it from other bacteria speces. It has the sequence:

| SEQ ID No. 8: | |
|---|---|
| ACCACAAGAC ATGCATCCCG TG | 22 |

It is conjugated with alkaline phosphatase as described in the preceding example. A third oligonucletide dTB1 (SEQ ID No. 6), complementary to nucleotides 253 to 281 of *M. tuberculosis* and whose role is to facilitate the hybridization of the detection probe bovis310 by being contiguous to it, is also added in solution. Thus, in this example, the capture and detection sites are not contiguous.

The hybridization of the rRNAs of the bacterial strains tested was carried out according to the procedure described in Example 2 except for two exceptions:

The extraction of the target rRNA is carried out according to the basic procedure for the extraction of RNA from Gram-positive bacteria which is described in "Current Protocols in Molecular Biology" 1987, Ausubel FM et al., Wiley interscience, New York.

The oligonucleotide dTB1 is added to the cuvette containing the alkaline phosphatase-labelled detection probe (Bovis310) at the concentration of 1 ng/ml.

The signal obtained by sandwich hybridization with the capture oligonucleotide E220 and the same capture oligonucleotide coupled to the bipolymer (conjugate CJOA, Table 4) was compared. The results are presented in Table 6 on various Mycobacterium strains.

TABLE 6

| | | INTENSITY OF DETECTION[b] | |
|---|---|---|---|
| STRAIN[a] | | E220 | Bipolymer-E220 Conjugate CJOA |
| *M. tuberculosis* | A 198 | 91 | 3939 |
| | A 216 [NCTC 7417] | 162 | 7778 |
| *M. bovis* | A 222 | 224 | 7818 |
| *M. bovis* BCG | A 223 | 278 | 7071 |
| *M. intracellulare* | A 227 [ATCC 35764] | 18 | 62 |
| *M. flavescens* | A 234 | 16 | 45 |
| *M. smegmatis* | A 251 | 11 | 25 |

[a]: the numbering of the strains is an internal reference of the applicant. For the reference strains, the code is indicated in brackets with the organization possessing them. The other strains were characterized by conventional phenotype methods.
[b]: expressed in relative fluorescence units (RFU).

Thus, Example 3 shows that the detection probe is specific for the strains of the tuberculosis complex, for it was verified that the rRNAs extracted from the other mycrobacteria strains were indeed available for the hybridization. Furthermore, an increase in signal is observed with the bipolymer-capture E220 conjugate compared with E220 in capture alone. The average factor for increase of the signal is 35.

EXAMPLE 4

Use of a capture oligonucleotide-bipolymer conjugate and comparison with a system where the capture consists of the oligonucleotide alone The model is the detection by hybridization of the taxonomic group "tuberculosis complex". The target is the 16S ribosomal RNA of this group. The capture probe dTB1 (SEQ ID No. 6) coupled to the bipolymer is complementary to the nucleotides 253 to 281 of the *Mycobacterium tuberculosis* 16S sequence determined by Suzuki Y., Nagata A., Oho Y. and Yamada T. (1988), J. Bacteriol., 170, pages 2886–2889. The detection probe bovis308 consists of the sequence specific for the tuberculosis complex taxonomic group covering *M. tuberculosis*, *M. bovis*, *M. bovis* BCG, *M. africanum*, *M. microti* and thus differentiates it from other bacterial species. It has the sequence (coordinates 281–300):

| SEQ ID. No. 9: | |
|---|---|
| ACCACAAGAC ATGCATCCCG | 20 |

It is conjugated with alkaline phosphatase as described earlier. The hybridization of the rRNAs of the bacterial strains tested was carried out according to the procedure described in Example 2, except for the extraction of the target rRNA carried out according to the basic procedure for the extraction of RNA from Gram-positive bacteria which is described in "Current Protocols in Molecular Biology" 1987, Ausubel FM et al., Wiley interscience, New York.

The signals obtained by sandwich hybridization with the capture oligonucleotide dTB1 and with the same capture oligonucleotide coupled to the bipolymer (conjugate CJOF, Table 4) were compared. The results are presented in Table 7.

TABLE 7

| | | INTENSITY OF DETECTION[b] | |
|---|---|---|---|
| STRAINS[a] | Strain No. | dTB1 | Bipolymer-dTB1 Conjugate CJOF |
| *M. tuberculosis* | C 001 | 71 | 3905 |
| | C 002 | 135 | 4485 |
| | C 003 | 120 | 4062 |
| | C 120 | 210 | 11437 |
| *M. bovis* BCG | A 221 [ATCC 19210] | 168 | 7818 |
| *M. avium/ intracellulare* | A 227 [ATCC 35764] | 12 | 15 |
| | C 080 | 10 | 9 |
| | C 081 | 11 | 8 |
| *M. flavescens* | C 095 | 11 | 7 |
| *M. smegmatis* | A 251 | 8 | 8 |

[a]: the numbering of the strains is internal to the applicant. For the strains deposited, the code is indicated in brackets with the organization for deposition. The other strains were characterized by conventional phenotype methods.
[b]: expressed in relative fluorescence units (RFU)

Thus, Example 4 shows that a significant rise in signal is produced with the oligonucleotide-bipolymer conjugate in capture and for a system of sequences different from Example 3.

This increase in sensitivity does not occur at the expense of specificity since this system makes it possible to distinguish species close to the genus Mycobacterium.

EXAMPLE 5

Use of a capture oligonucleotide-bipolymer conjugate and comparison with a system in which the capture consists of the oligonucleotide alone. The target to be detected consists of a PCR fragment:

A PCR (polymerase chain reaction) is carried out according to the standard procedure as described in "PCR PROTOCOLS, A guide to methods and applications", edited by M. A. Innis, D. H. Gelfand, J. J. Sninsky, T. J. White, Academic Press, on a DNA plasmid pBR322 (SIGMA, reference D4904) containing 4363 base pairs, in solution in 10 mM Tris buffer pH 8.0. The two primers used for the amplification are TEM1 (SEQ ID No. 10) and TEM2 (SEQ ID No. 11):

| SEQ ID No. 10: | |
|---|---|
| CCCCGAAGCG TTTTC | 15 |
| SEQ ID No. 11: | |
| CGGTATGGTT TGCTGCT | 17 |

The PCR fragment produced is checked on a 5% acrylamide gel. It contains 347 base pairs.

100 µl of a solution of the oligonucleotide 1844 (SEQ ID No. 1) at the concentration of 1 ng/µl (0.15 µM) in 3×PBS buffer (0.15M sodium phosphate, 0.45M sodium chloride pH 7.5) are deposited in a NUNC polystyrene microtitre plate reference 439454. The incubation is carried out for two hours at the temperature of 37° C.

In parallel, 100 µl of oligonucleotide-bipolymer conjugate (CJOG, Table 4) at the same oligonucleotide concentration of 1 ng/µl in 3×PBS are deposited in another plate. The plate is incubated for two hours at 37° C. The plate is then emptied and washed with 3×300 µl of PBS-Tween (50 mM sodium phosphate, 150 µM sodium chloride containing 0.5 ml/l of Tween 20 reference MERCK 822184).

The PCR fragment is denatured before use by mixing 100 µl of solution from the PCR with 10 µl of 2N sodium hydroxide. The whole is neutralized 5 minutes later by the addition of 10 µl of 2N acetic acid.

100 µl of the dilutions of the denatured PCR fragment, in PBS-salmon buffer (150 mM sodium phosphate, pH 7.0, 450 mM NaCl+0.1 mg/ml salmon sperm DNA (Sigma D 9156)) are added to the wells of the microtitre plate. The plate is incubated for one hour at 37° C. and then washed with 3×300 µl of PBS-Tween.

Into each well of the plate are added 100 µl (0.1 ng/µl of oligonucleotides in PBS-salmon buffer) of detection probe D1 (SEQ ID No. 12) coupled to alkaline phosphatase as described in Example 2.

| SEQ ID No. 12: | |
|---|---|
| CGCTTTTTTG CACAACATGG GGGATCATG | 29 |

The plate is incubated for one hour at 37° C. and then washed with 3×300 µl of PBS-Tween.

Into each well of the plate are added 100 µl of PNPP substrate (para-nitrophenylphosphate sold by SIGMA under the reference N2765) prepared as follows: a pastille of 20 mg of substrate is taken up in 10 ml of 1M diethanolamine buffer, 0.5 mM MgCl$_2$, pH 9.8. After 20 min of reaction, the enzymatic activity is blocked with 100 µl of 1N NaOH.

The reading of the optical density is carried out at a wavelength of 402 nm on a BIOMERIEUX AXIA MICROREADER plate reader.

The results obtained are summarized in Table 8 below.

TABLE 8

| PCR dilution | 1844 | Bipolymer-1844 CJOG |
|---|---|---|
| 0 | 35 | 70 |
| 1/100,000 | 55 | 280 |
| 1/10,000 | 70 | 490 |
| 1/1,000 | 120 | 864 |
| 1/100 | 335 | 1750 |
| 1/10 | 1200 | 2255 |

The values obtained correspond to the units of optical density measured on an AXIA MICROREADER apparatus (AXIA trademark-BIOMERIEUX).

There is indeed sensitivity gain to detect a PCR fragment using, as capture probe, an oligonucleotide-bipolymer conjugate compared with an oligonucleotide. This sensitivity gain is not achieved at the expense of specificity since the signal obtained for the PCR dilution 0, which corresponds to the absence of target to be detected, gives a weaker signal than the lowest dilution of 1/100,000.

EXAMPLE 6

Use of a Capture Oligonucleotide-bipolymer Conjugate in Immunoassays

Detection of alpha-foetoprotein (AFP) by the sandwich procedure. Comparison with the conventional sandwich method where the capture antibody is adsorbed directly onto the solid support and the method using a bipolymer-oligonucleotide conjugate adsorbed on the solid phase, the said oligonucleotide being complementary to a second oligonucleotide covalently coupled to the capture antibody.

100 µl of a solution of the anti(α-foetoprotein) antibody (reference P7B10B7, BIOMERIEUX) diluted to the concentration of 10 µg/ml in sodium carbonate buffer (Na$_2$CO$_3$ PROLABO reference 27771290-NaBCO$_3$ PROLABO reference 27778293) 50 mM, pB 9.6, are deposited into a NUNC polystyrene microtitre plate reference 439454. The incubation is carried out for two hours at the temperature of 37° C.

In parallel, 100 µl of conjugate (CJOB, Table 4) between the oligonucleotide pBP5 (SEQ ID No. 3) coupled to a bipolymer in 3×PBS buffer are deposited in another plate. The incubation is carried out for two hours at the temperature of 37° C. After 3 washes with 300 µl of PBS-Tween buffer, 100 µl of oligonucleotide CpBP5 (SEQ ID No. 13) coupled to the anti-AFP antibody. (reference P7H10B7 BIOMERIEUX) diluted in PBS-salmon buffer are added to the wells of the microtitre plate.

The coupling between the antibody and the oligonucleotide CpBP5 is carried out according to the same method as described for the oligonucleotide-peroxidase coupling in Patent WO 91/19812.

| SEQ ID No. 13: | |
|---|---|
| TACCGTTCTC ATATAGCTCA TC | 22 |

The plate is incubated for one hour at 37° C. and then washed with 3×300 µl of PBS-Tween.

50 µl of alpha-foetoprotein antigen (AFP) (marketed by BEERING under the reference OTOD 02/03) diluted in PBS Tween buffer containing 10% horse serum are then added to each well of the two plates. To estimate the sensitivity, the AFP concentrations vary from 0 to 100 μg/ml. 50 μl of anti-AFP antibody (reference P3F11G9, BIOMERIEUX) coupled to peroxidase according to conventional methods, at the concentration of 0.3 mg/ml in PBS Tween buffer containing 10% horse serum, are then added. The plate is incubated for one hour at 37° C. and then washed with 3 times 300 μl of PBS-Tween.

Into each well of the plate are added 100 μl of OPD substrate (ortho-phenylenediamine sold by SIGMA under the reference P7288) and prepared as follows: a pastille of 20 mg of substrate is taken up in 10 ml of citrate buffer pH 4.93 (0.055M citric acid, 0.1M $Na_2HPO_4$). After 30 min of reaction at 37° C., the enzymatic activity is blocked with 100 μl of 1N $H_2SO_4$.

The reading of the optical density is carried out at a wavelength of 492 nm on an AXIA MICROREADER plate reader.

The results obtained are summarized in Table 9.

TABLE 9

| Concentration of AFP in μg/ml | Antibody directly adsorbed | Antibody attached by the bipolymer/ oligonucleotide |
|---|---|---|
| 0 | 120 | 230 |
| 1 | 125 | 280 |
| 2.5 | 150 | 430 |
| 5 | 150 | 515 |
| 10 | 150 | 905 |
| 50 | 150 | 2500 |
| 100 | 190 | 2500 |

The values obtained correspond to the units of optical density measured on the AXIA MICROREADER.

The results obtained show a very high increase in the sensitivity of the test with the use of the bipolymer-oligonucleotide to attach the capture antibody. A detection of 2.5 μg/ml of alpha-foetoprotein is possible with the amplification system using the bipolymer-oligonucleotide. The factor for increase in the signal obtained is greater than 10.

We claim:

1. Device for capturing a target molecule for the purpose of detecting it and/or assaying it, comprising a water-soluble conjugate immobilized on a solid support by adsorption, said conjugate resulting from a covalent coupling of a polymer with a plurality of molecules of a ligand, wherein said polymer is an N-vinylpyrrolidone copolymer.

2. Device according to claim 1, wherein the copolymer results from copolymerization of an N-vinyl pyrrolidone monomer and a second monomer that establishes a covalent coupling between the ligand and the copolymer.

3. Device according to claim 2, wherein the second monomer contains a reactive functional group or an activable functional group that forms a covalent bond between the copolymer and the ligand, said reactive functional group being selected from the group consisting of aldehyde, epoxy, haloalkyl, primary amine, thiol, maleimide and ester functional groups, and said activable functional group being selected from the group consisting of carboxyl and hydroxyl functional groups.

4. Device according to claim 3, wherein said reactive functional group is a N-hydroxysuccinimide ester functional group.

5. Device according to claim 2, wherein the second monomer is N-acryloxysuccinimide.

6. Device according to claim 1, wherein said copolymer contains from 25 to 70%, in units, of N-vinylpyrrolidone units.

7. Device according to claim 1, wherein said ligand binds with an anti-ligand to form a ligand/anti-ligand capture complex.

8. Device according to claim 7, wherein said anti-ligand is the target molecule.

9. Device according to claim 8, wherein said complex is selected from the group consisting of antigen/antibody, antibody/hapten, hormone/receptor, and chelator/chelated molecule, polynucleotide/polynucleotide and polynucleotide/nucleic acid.

10. Device according to claim 7, wherein said ligand is a polynucleotide containing from 5 to 100 nucleotides.

11. Device according to claim 1, wherein the solid support is selected from the group consisting of a microtitre plate, a sheet, a cone, a tube, a well and a bead.

12. A process for capturing a target molecule, comprising:

bringing a device according to claim 8 into contact with the target molecule in solution in an aqueous medium under conditions permitting the formation of a complex between the ligand and the target; and allowing said complex to form.

13. Kit for capturing a target molecule for the purpose of detecting and/or assaying it, comprising: a container containing (1) a water-soluble conjugate immobilized on a solid support by adsorption, said conjugate resulting from a covalent coupling of a polymer with a plurality of molecules of a ligand, wherein said polymer is an N-vinyl pyrrolidone copolymer, and (2) a bifunctional reagent comprising an anti-ligand group bonded with a partner group, wherein said anti-ligand group binds with the ligand to form a complex and said partner group binds with the target to form a partner/target complex.

14. Kit according to claim 13, wherein the anti-ligand group binds with the ligand to form a complex selected from the group consisting of antigen/antibody, antibody/hapten, hormone/receptor, polynucleotide/polynucleotide hybrid, polynucleotide/nucleic acid hybrid, chelator/chelated molecule, biotin/streptavidin and lectin/sugar complexes.

15. A process for capturing a target molecule, comprising:

providing a device comprising: (1) a water-soluble conjugate immobilized on a solid support by adsorption, said conjugate resulting from a covalent coupling of an N-vinylpyrrolidone copolymer with a plurality of molecules of a ligand, and (2) a bifunctional reagent comprising an anti-ligand group bonded with a partner group, wherein said anti-ligand group is attached to a ligand of the water-soluble conjugate to form a complex;

bringing the device into contact with the target molecule in solution in an aqueous medium under conditions permitting the formation of a complex between the partner group and the target; and allowing said complex between the partner and the target to form.

* * * * *

UNITED STATES PATENT AND TRADEMARK OFFICE
CERTIFICATE OF CORRECTION

PATENT NO. : 5,723,344
DATED : March 3, 1998
INVENTOR(S) : Claude MABILAT, Philippe CROS, Bernard MANDRAND, Marie-Helene CHARLES, Marie-Noelle EROUT, Christian PICHOT It is certified that error appears in the above-indentified patent and that said Letters Patent is hereby corrected as shown below:

On the title page: in item [75], line 2, change "Lyons" to --Lyon--.

Signed and Sealed this

Twenty-sixth Day of May, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: cDNA to rRNA ( x i ) SEQUENCE DESCRIPTION: SEQ ID NO:1:

TCATCCACCT GGCATTGGAC TGCCATAACC ATGAGTG        37

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA to rRNA ( x i ) SEQUENCE DESCRIPTION: SEQ ID NO:2:

TCTAATCCTG TTTGCTCCCC        20

( 2 ) INFORMATION FOR SEQ ID NO:3:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA to rRNA ( x i ) SEQUENCE DESCRIPTION: SEQ ID NO:3:

GATGAGCTAT ATGAGAACGG TA                                                     22

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA to rRNA ( x i ) SEQUENCE DESCRIPTION: SEQ ID NO:4:

TTAACTTTAC TCCCTTCCTC CCCGCTG                                                27

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA to rRNA ( x i ) SEQUENCE DESCRIPTION: SEQ ID NO:5:

TCAATGAGCA AAGGTA                                                            16

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA to rRNA ( x i ) SEQUENCE DESCRIPTION: SEQ ID NO:6:

GGTCCTATCC GGTATTAGAC CCAGTTTCC                                              29

( 2 ) INFORMATION FOR SEQ ID NO:7:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: cDNA to rRNA ( x i ) SEQUENCE DESCRIPTION: SEQ ID NO:7:

TTTCAGCGGG GAGGAAGGGA GTAAAGTTAA TACCTTTGCT CATTGACGTT ACCCGCAGAA            60

G                                                                            61

( 2 ) INFORMATION FOR SEQ ID NO:8:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to rRNA ( x i ) SEQUENCE DESCRIPTION: SEQ ID NO:8:

ACCACAAGAC ATGCATCCCG TG                                                    22

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to rRNA ( x i ) SEQUENCE DESCRIPTION: SEQ ID NO:9:

ACCACAAGAC ATGCATCCCG                                                       20

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA to rRNA ( x i ) SEQUENCE DESCRIPTION: SEQ ID NO:10:

CCCCGAAGCG TTTTC                                                            15

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to rRNA ( x i ) SEQUENCE DESCRIPTION: SEQ ID NO:11:

CGGTATGGTT TGCTGCT                                                          17

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA to rRNA ( x i ) SEQUENCE DESCRIPTION: SEQ ID NO:12:

CGCTTTTTG CACAACATGG GGGATCATG                                              29

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to rRNA ( x i ) SEQUENCE DESCRIPTION: SEQ ID NO:13:

TACCGTTCTC ATATAGCTCA TC                                                    22